US010654779B2

(12) United States Patent
Miyauchi et al.

(10) Patent No.: US 10,654,779 B2
(45) Date of Patent: May 19, 2020

(54) SUBSTITUTED BIS(TRIFLUOROVINYL)BENZENE COMPOUND

(71) Applicant: TOSOH FINECHEM CORPORATION, Shunan-shi, Yamaguchi (JP)

(72) Inventors: Hideki Miyauchi, Shunan (JP); Norihisa Kondo, Shunan (JP); Noritaka Nagasaki, Shunan (JP)

(73) Assignee: TOSOH FINECHEM CORPORATION, Shunan-Shi, Yamaguchi (JP)

( * ) Notice: Subject to any disclaimer, the term of this patent is extended or adjusted under 35 U.S.C. 154(b) by 0 days.

(21) Appl. No.: 16/336,792

(22) PCT Filed: Sep. 6, 2017

(86) PCT No.: PCT/JP2017/032115
§ 371 (c)(1),
(2) Date: Mar. 26, 2019

(87) PCT Pub. No.: WO2018/061677
PCT Pub. Date: Apr. 5, 2018

(65) Prior Publication Data
US 2020/0017429 A1    Jan. 16, 2020

(30) Foreign Application Priority Data
Sep. 27, 2016    (JP) .................................. 2016-188114

(51) Int. Cl.
| C07C 22/08 | (2006.01) |
| C07C 17/32 | (2006.01) |
| C07C 25/24 | (2006.01) |
| C07C 41/22 | (2006.01) |
| C07C 43/225 | (2006.01) |
| C07B 61/00 | (2006.01) |

(52) U.S. Cl.
CPC .............. C07C 22/08 (2013.01); C07C 17/32 (2013.01); C07C 25/24 (2013.01); C07C 41/22 (2013.01); C07C 43/225 (2013.01)

(58) Field of Classification Search
None
See application file for complete search history.

(56) References Cited

U.S. PATENT DOCUMENTS 5,159,038 A * 10/1992 Babb .................... C07C 17/269
526/242
2017/0226255 A1    8/2017    Shimizu et al.

FOREIGN PATENT DOCUMENTS

| JP | H8-509765 A | 10/1996 |
| JP | 10-195181 A | 7/1998 |
| JP | 3022921 B2 | 1/2000 |
| WO | 90/15082 A1 | 12/1990 |
| WO | 94-25547 A1 | 11/1994 |

(Continued)

OTHER PUBLICATIONS

Ford et al., "A novel 1,3,5-tris(α,β,β-trifluorovinyl)benzene monomer," *Chemical Communications*, 20: 2596-2597, 2003.

(Continued)

*Primary Examiner* — Rosalynd A Keys
(74) *Attorney, Agent, or Firm* — Seed IP Law Group LLP

(57) ABSTRACT

There is provided a substituted bis(trifluorovinyl)benzene compound that is excellent in heat stability and is industrially useful, and a method for producing the same. There are used a substituted bis(trifluorovinyl)benzene compound represented by general formula (1);

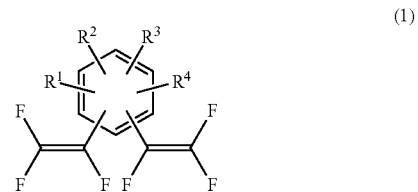

(1)

and a method for producing a substituted bis(trifluorovinyl)benzene compound, comprising the step of reacting in the presence of a catalyst (such as palladium) a bishalobenzene derivative represented by general formula (3)

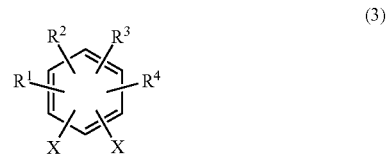

(3)

and a compound obtained by reacting 1,1,1,2-tetrafluoroethane, a zinc halide, and an organolithium compound and represented by general formula (4),

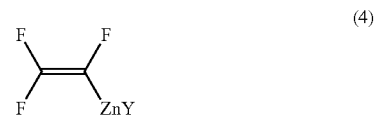

(4)

to thereby obtain a substituted bis(trifluorovinyl)benzene compound represented by general formula (1).

20 Claims, No Drawings

(56) References Cited

FOREIGN PATENT DOCUMENTS

WO 2015/046569 A1 4/2015
WO 2016/017187 A1 2/2016

OTHER PUBLICATIONS

Jiang et al., "The spin-delocalization substituent parameter σjj. part 10. The spin-delocalizing abilities of the para-trifluorovinyl and para-acetoxy groups. Synthesis of para-trifluorovinyl-, para-vinyl- and para-acetoxy-α,β,β-trifluorostyrenes," *Journal of Fluorine Chemistry*, 79:173-178, 1996.
*Journal of the American Chemical Society*, 95: 7923-7925, 1973.

* cited by examiner

SUBSTITUTED BIS(TRIFLUOROVINYL)BENZENE COMPOUND

TECHNICAL FIELD

The present invention relates a novel substituted bis(trifluorovinyl)benzene compound that is excellent in heat stability and useful as a starting material for polymers.

BACKGROUND ART

Styrene compounds, which have a single vinyl group on its benzene ring thereof, and divinylbenzene compounds, which have two vinyl groups on its benzene ring, have long been used as a starting material for ion exchange resins. An example of compounds obtained by replacing hydrogen atoms of the vinyl group of these compounds with fluorine atoms is (trifluorovinyl)benzene, which is an industrially useful compound as a functional material, such as an electrolyte membrane for fuel cells and a resist material, or an intermediate for producing a pharmaceutical or an agrochemical.

There are reports on an instance of synthesis of bis(trifluorovinyl)benzene (see, for example, Non-Patent Document 1), but there are no instances of industrial application using it. This is probably because bis(trifluorovinyl)benzene has poor heat stability.

For example, it is reported that heating (trifluorovinyl)benzene easily results in cyclic dimerization thereof to give a perfluorocyclobutane compound (see, for example, Non-Patent Documents 1 and 2). Also there are reports on an instance of synthesis of a polymer through the cyclic dimerization (see, for example, Patent Documents 1 and 2), but the cyclic dimerization proceeds even in common polymerization conditions to thereby sometimes cause problems in intended polymerization. Long-term storage stability is also a serious problem. Therefore, there is a need for a bis(trifluorovinyl)benzene compound excellent in heat stability.

PRIOR ART DOCUMENT

Patent Document

Patent Document 1: JP 3022921 B
Patent Document 2: JP H8-509765 A

Non-Patent Document

Non-Patent Document 1: J. Fluorine. Chem., 1996, vol. 79, p. 173-178
Non-Patent Document 2: Journal of the American Chemical Society, 1973, vol. 95, p. 7923-7925

SUMMARY OF THE INVENTION

Problems to be Solved by the Invention

As mentioned above, bis(trifluorovinyl)benzene has poor heat stability and is thus difficult to industrially utilize as a starting material for polymers or an additive. Indeed, the present inventors have studied the stability of bis(trifluorovinyl)benzene and, as a result, found that it has poor heat stability and is difficult to industrially use.

Thus, an object of the present invention is to provide a substituted bis(trifluorovinyl)benzene compound that is excellent in heat stability and industrially useful, and a method for producing the same.

Means for Solving the Problems

As a result of intensive studies, the present inventors have found that a substituted bis(trifluorovinyl)benzene compound having a specific substituent is excellent in heat stability, and thus have completed the present invention.

Specifically, the present invention provides a substituted bis(trifluorovinyl)benzene compound represented by general formula (1):

[Formula 1]

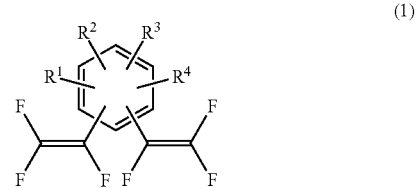

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions of the benzene ring to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

The substituted bis(trifluorovinyl)benzene compound represented by general formula (1) meets any of the following conditions (i) to (iii) for the trifluorovinyl group thereof.

(i) When the two trifluorovinyl groups in the substituted bis(trifluorovinyl)benzene compound are in para positions to each other, e.g., 1,4-positions, on the benzene ring, 6-position and/or 2-position, which are ortho position to the trifluorovinyl group at 1-position, and 3-position and/or 5-position, which are ortho position to the trifluorovinyl group at 4-position are each substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom (hereinafter, the group consisting of these substituent groups that do not encompass a hydrogen atom is referred to as "substituent groups excluding hydrogen), and the other positions may be substituted with a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom (hereinafter, the group consisting of these substituent groups that encompass a hydrogen atom is referred to as "substituent groups including hydrogen").

(ii) When the two trifluorovinyl groups in the substituted bis(trifluorovinyl)benzene compound are in meta positions to each other, e.g., 1,3-positions, 2-position, which is ortho position to the trifluorovinyl group at 1-position and also ortho position to the other trifluorovinyl group at 3-position, is substituted with any of the substituent groups excluding hydrogen described for condition (i) while the other positions may be substituted with any of the substituent groups including hydrogen, or 2-position is occupied by a hydrogen atom provided that 4-position and 6-position are substituted with any of the substituent groups excluding hydrogen while the other positions may be substituted with any of the substituent groups including hydrogen.

(iii) When the two trifluorovinyl groups in the substituted bis(trifluorovinyl)benzene compound are in ortho positions to each other, e.g., 1,2-positions, which means that ortho position of one trifluorovinyl group is substituted with the other trifluorovinyl group, 3,4,5,6-positions may be substituted with any of the substituent groups including hydrogen; provided that $R^1$ to $R^4$ are not all hydrogen atoms.

Conditions (i) to (iii) described above also apply to the method for producing a substituted bis(trifluorovinyl)benzene compound represented by general formula (1) described later.

The present invention also provides a substituted bis(trifluorovinyl)benzene compound represented by general formula (2):

[Formula 2]

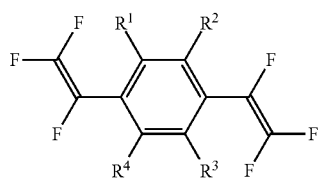

(2)

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions of the benzene ring to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

Specifically, for each of the two trifluorovinyl groups in the substituted bis(trifluorovinyl)benzene compound of general formula (2), 2- and 5-positions, or 2- and 3-positions, which are all ortho positions, are substituted with any of substituent groups excluding hydrogen described for condition (i), and the other positions may be substituted any of substituent groups including hydrogen described for condition (i).

The present invention also provides the substituted bis(trifluorovinyl)benzene compound wherein in the substituted bis(trifluorovinyl)benzene compound represented by general formula (1) or (2), at least one of ortho positions to a trifluorovinyl group is substituted with a methyl group, a trifluoromethyl group, a difluoromethyl group, a pentafluoroethyl group, a methoxy group, or a fluorine atom.

The present invention also provides the substituted bis(trifluorovinyl)benzene compound wherein the substituted bis(trifluorovinyl)benzene compound represented by general formula (2) is 1,4-bis(trifluorovinyl)-2,3,5,6,-tetramethylbenzene, 1,4-bis(trifluorovinyl)-2,5-dimethylbenzene, 1,4-bis(trifluorovinyl)-2,5-difluorobenzene, or 1,4-bis(trifluorovinyl)-2,5-bis(trifluoromethyl)benzene.

The present invention also provides a method for producing a substituted bis(trifluorovinyl)benzene compound, comprising the step of reacting in the presence of a catalyst (such as palladium)
a bishalobenzene derivative represented by general formula (3):

[Formula 3]

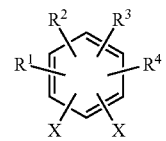

(3)

wherein X is iodine and/or bromine,
$R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to an X group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom; and a compound obtained by reacting 1,1,1,2-tetrafluoroethane, a zinc halide, and an organolithium compound and represented by general formula (4):

[Formula 4]

(4)

wherein Y represents chlorine, bromine, or iodine, to obtain a substituted bis(trifluorovinyl)benzene compound represented by general formula (6):

[Formula 6]

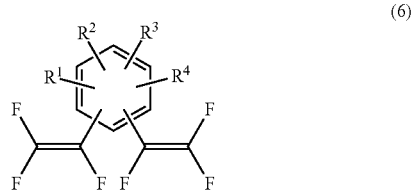

(6)

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

The substituted bis(trifluorovinyl)benzene compound represented by general formula (1) and the bishalobenzene derivative represented by general formula (3) as a starting material thereof meet any of following conditions (i) to (iii) for the trifluorovinyl group thereof. This also applies to general formula (5) described later.

(i) When the two trifluorovinyl groups in the substituted bis(trifluorovinyl)benzene compound are in para positions to each other, e.g., 1,4-positions, on the benzene ring, 6-position and/or 2-position, which are ortho position to the trifluorovinyl group at 1-position, and 3-position and/or 5-position, which are ortho position to the trifluorovinyl group at 4-position are each substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom (hereinafter, the group consisting of these substituent groups that do not encompass a hydrogen atom is referred to as "substituent groups excluding hydrogen), and the other positions may be substituted with a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom (hereinafter, the group consisting of these substituent groups encompass a hydrogen atom is referred to as "substituent groups including hydrogen").

(ii) When the two trifluorovinyl groups in the substituted bis(trifluorovinyl)benzene compound are in meta positions to each other, e.g., 1,3-positions, 2-position, which is ortho position to the trifluorovinyl group at 1-position and also ortho position to the other trifluorovinyl group at 3-position, is substituted with any of the substituent groups excluding hydrogen described for condition (i) while the other positions may be substituted with any of the substituent groups including hydrogen, or 2-position is occupied by a hydrogen atom provided that 4-position and 6-position are substituted with any of the substituent groups excluding hydrogen while the other positions may be substituted with any of the substituent groups including hydrogen.

(iii) When the two trifluorovinyl groups in the substituted bis(trifluorovinyl)benzene compound are in ortho positions to each other, e.g., 1,2-positions, which means that ortho position of one trifluorovinyl group is substituted with the other trifluorovinyl group, 3,4,5,6-positions may be substituted with any of the substituent groups including hydrogen; provided that $R^1$ to $R^4$ are not all hydrogen atoms.

The present invention also provides a method for producing a substituted bis(trifluorovinyl)benzene compound, comprising the step of reacting in the presence of a catalyst (such as palladium)

a 1,4-bishalobenzene derivative represented by general formula (5):

[Formula 5]

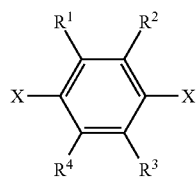

(5)

wherein X is iodine and/or bromine,
$R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to an X group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom; and
a compound obtained by reacting 1,1,1,2-tetrafluoroethane, a zinc halide, and an organolithium compound and represented by general formula (4):

[Formula 4]

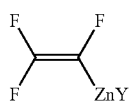

(4)

wherein Y represents chlorine, bromine, or iodine, to obtain a substituted bis(trifluorovinyl)benzene compound represented by general formula (7):

[Formula 7]

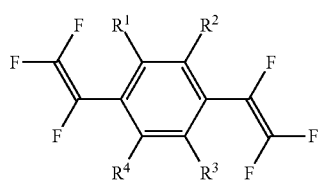

(7)

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

For each of the two substituent groups represented by X on the benzene ring in general formula (5), 2- and 5-positions, or 2- and 3-positions, which are all ortho positions, are substituted with any of substituent groups excluding hydrogen described for condition (i), and the other positions may be substituted with any of substituent groups including hydrogen described for condition (i).

For each of the two trifluorovinyl groups of the substituted bis(trifluorovinyl)benzene compound represented by general formula (2), 2- and 5-positions, or 2- and 3-positions, which are all ortho positions, are substituted with any of substituent groups excluding hydrogen described for condition (i), and the other positions may be substituted with any of substituent groups including hydrogen described for condition (i).

The present invention also provides the method for producing a substituted bis(trifluorovinyl)benzene compound wherein in the substituted bis(trifluorovinyl)benzene compound represented by general formula (1) or (2), at least one of ortho positions to a trifluorovinyl group is substituted with a methyl group, a trifluoromethyl group, a difluoromethyl group, a pentafluoroethyl group, a methoxy group, or a fluorine atom.

The present invention also provides the method for producing a substituted bis(trifluorovinyl)benzene compound wherein the substituted bis(trifluorovinyl)benzene compound represented by general formula (2) is 1,4-bis(trifluorovinyl)-2,3,5,6,-tetramethylbenzene, 1,4-bis(trifluorovinyl)-2,5-dimethylbenzene, 1,4-bis(trifluorovinyl)-2,5-difluorobenzene, or 1,4-bis(trifluorovinyl)-2,5-bis(trifluoromethyl)benzene.

The present invention also provides the substituted bis(trifluorovinyl)benzene compound wherein the substituted bis(trifluorovinyl)benzene compound represented by general formula (1) or (2) is 1,4-bis(trifluorovinyl)-2,5-dimethoxybenzene.

The present invention also provides the method for producing a substituted bis(trifluorovinyl)benzene compound wherein the substituted bis(trifluorovinyl)benzene compound represented by general formula (6) or (7) is 1,4-bis(trifluorovinyl)-2,5-dimethoxybenzene.

The present invention also provides a substituted bis(trifluorovinyl)benzene compound represented by general formula (8) or (9):

[Formula 8]

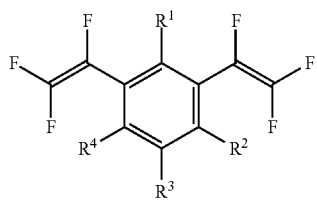
(8)

[Formula 9]

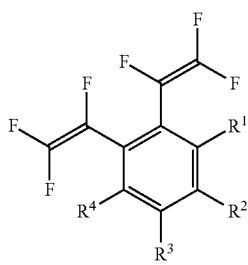
(9)

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions of the benzene ring to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

General formula (8) meets condition (ii), and general formula (9) meets condition (iii).

The present invention also provides the substituted bis(trifluorovinyl)benzene compound wherein in the substituted bis(trifluorovinyl)benzene compound represented by general formula (1), or (8) or (9), at least one of ortho positions to a trifluorovinyl group is substituted with a methyl group, a trifluoromethyl group, a difluoromethyl group, a pentafluoroethyl group, a methoxy group, a difluoromethoxy group, or a fluorine atom.

The present invention also provides the substituted bis(trifluorovinyl)benzene compound wherein the substituted bis(trifluorovinyl)benzene compound represented by general formula (1), or (8) or (9) is 1,3-bis(trifluorovinyl)-4,6-dimethylbenzene, 1,3-bis(trifluorovinyl)-2-methylbenzene, 1,3-bis(trifluorovinyl)-5-fluoro-2-difluoromethylbenzene, 1,2-bis(trifluorovinyl)-4,5-difluorobenzene, 1,2-bis(trifluorovinyl)-3,5-difluorobenzene.

The present invention also provides a method for producing a substituted bis(trifluorovinyl)benzene compound, comprising the step of reacting in the presence of a catalyst (such as palladium)
a 1,3-bishalobenzene derivative represented by general formula (10) or (11):

[Formula 10]

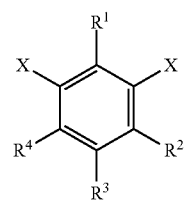
(10)

[Formula 11]

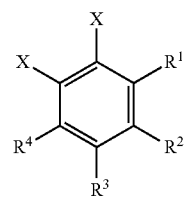
(11)

wherein X is iodine and/or bromine,
$R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to an X group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom; and
a compound obtained by reacting 1,1,1,2-tetrafluoroethane, a zinc halide, and an organolithium compound and represented by general formula (4):

[Formula 4]

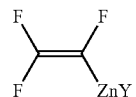
(4)

wherein Y represents chlorine, bromine, or iodine, to obtain a substituted bis(trifluorovinyl)benzene compound represented by general formula (12) or (13):

[Formula 12]

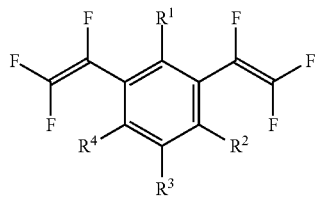

[Formula 13]

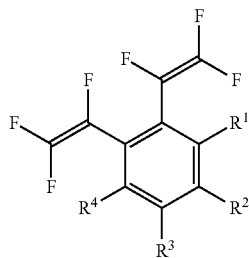

wherein $R^1$ to $R^4$ are as defined for formula (8) or (9).

General formula (10) meets condition (ii), which formula represents a starting material corresponding to the compound represented by general formula (12). General formula (11) meets condition (iii), which formula represents a starting material corresponding to the compound represented by general formula (13).

The present invention also provides the method for producing a substituted bis(trifluorovinyl)benzene compound wherein in the substituted bis(trifluorovinyl)benzene compound represented by general formula (6), (12), or (13), at least one of ortho positions to a trifluorovinyl group is substituted with a methyl group, a trifluoromethyl group, a difluoromethyl group, a pentafluoroethyl group, a methoxy group, a difluoromethoxy group, or a fluorine atom.

The present invention also provides the method for producing a substituted bis(trifluorovinyl)benzene compound wherein the substituted bis(trifluorovinyl)benzene compound represented by general formula (6), (12) or (13) is 1,3-bis(trifluorovinyl)-4,6-dimethylbenzene, 1,3-bis(trifluorovinyl)-2-methylbenzene, 1,3-bis(trifluorovinyl)-5-fluoro-2-difluoromethylbenzene, 1,2-bis(trifluorovinyl)-4,5-difluorobenzene, 1,2-bis(trifluorovinyl)-3,5-difluorobenzene.

Advantageous Effects of the Invention

According to the present invention, a substituted bis(trifluorovinyl)benzene compound that is excellent in heat stability and industrially useful can be provided.

According to the present invention, a method for producing such a substituted bis(trifluorovinyl)benzene compound can also be provided.

MODE FOR CARRYING OUT THE INVENTION

The present invention will be described in more details below.

<Substituted Bis(Trifluorovinyl)Benzene Compound of Present Invention>

As described above, the substituted bis(trifluorovinyl)benzene compound of the present invention is represented by general formula (1):

[Formula 1]

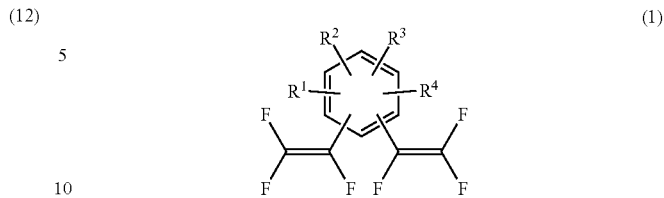

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions of the benzene ring to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

As described above, the substituted bis(trifluorovinyl) benzene compound of the present invention is represented by general formula (2):

[Formula 2]

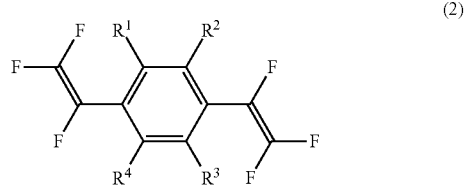

wherein $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions of the benzene ring to a trifluorovinyl group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

Specific examples of the substituted bis(trifluorovinyl)benzene compound of the present invention represented by general formula (1) or (2) are as follows.

Specifically, examples thereof include 1,4-bis(trifluorovinyl)-2,5-dimethylbenzene, 1,4-bis(trifluorovinyl)-2,5-bis(trifluoromethyl)benzene, 1,4-bis(trifluorovinyl)-2,5-bis(difluoromethyl)benzene, 1,4-bis(trifluorovinyl)-2,5-bis(pentafluoroethyl)benzene, 1,4-bis(trifluorovinyl)-2,5-bis(perfluorobutyl)benzene, 1,4-bis(trifluorovinyl)-2,5-dimethoxybenzene, 1,4-bis(trifluorovinyl)-2,5-bis(trifluoroethoxy)benzene, 1,4-bis(trifluorovinyl)-2,5-difluorobenzene, 1,4-bis(trifluorovinyl)-2,5-dichlorobenzene, 1,4-bis(trifluorovinyl)-2,3-dimethylbenzene, 1,4-bis(trifluorovinyl)-2,3,5-trimethylbenzene, 1,4-bis(trifluorovinyl)-2,3,5-trifluorobenzene, 1,4-bis(trifluorovinyl)-2,3,5,6-tetramethylbenzene, 1,4-bis(trifluorovinyl)-2,3,5,6-tetrafluorobenzene, 1,3-bis(trifluorovinyl)-4,6-dimethylbenzene, 1,3-bis(trifluorovinyl)-2,4-dimethylbenzene, 1,3-bis(trifluorovinyl)-2,5-dimethylbenzene, 1,3-bis(trifluorovinyl)-4,5,6-trimethylbenzene, 1,3-bis(trifluorovinyl)-2,4,5-trimethylbenzene, 1,3-bis(trifluorovinyl)-2,4,5,6-tetramethylbenzene, 1,3-bis(trifluorovinyl)-4,6-difluorobenzene, 1,3-bis(trifluorovinyl)-2,4,5,6-fluorobenzene, 1,3-bis(trifluorovinyl)-4-chloro-6-fluorobenzene, 1,3-bis(trifluorovinyl)-2-methylbenzene, 1,3-bis(trifluorovinyl)-2-fluorobenzene, 1,3-bis(trifluorovinyl)-5-fluoro-2-(trifluoromethyl)benzene, 1,3-bis(trifluorovinyl)-5-fluoro-2-(difluoromethyl)benzene, 1,3-bis(trifluorovinyl)-5-fluoro-2-(pentafluoroethyl)benzene, 1,2-bis(trifluorovinyl)-4,5-dimethylbenzene, 1,2-bis(trifluorovinyl)-3,6-dimethylbenzene, 1,2-bis(trifluorovinyl)-3,5-dimethylbenzene, 1,2-bis(trifluorovinyl)-4,5-difluorobenzene, 1,2-bis(trifluorovinyl)-3,5-difluorobenzene, 1,2-bis(trifluorovinyl)-3,4,5-trimethylbenzene, 1,2-bis(trifluorovinyl)-3,4,6-trimethylbenzene, 1,2-bis(trifluorovinyl)-3,4,5,6-tetramethylbenzene, and 1,2-bis(trifluorovinyl)-3,6-bis(chloromethyl)-4,5-dimethylbenzene.

<Method for Producing Substituted Bis(Trifluorovinyl) Benzene Compound of Present Invention>

As described above, the method for producing a substituted bis(trifluorovinyl)benzene compound of the present invention is a method comprising the step of reacting in the presence of a catalyst (such as palladium)

a bishalobenzene derivative represented by general formula (3):

[Formula 3]

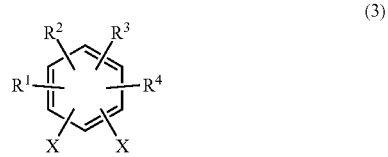

wherein X is iodine and/or bromine, $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to an X group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom; and a compound obtained by reacting 1,1,1,2-tetrafluoroethane, a zinc halide, and an organolithium compound and represented by general formula (4):

[Formula 4]

wherein Y represents chlorine, bromine, or iodine, to obtain a substituted bis(trifluorovinyl)benzene compound represented by general formula (1).

As described above, the method for producing a substituted bis(trifluorovinyl)benzene compound of the present invention is a method comprising the step of reacting in the presence of a catalyst (such as palladium)

a 1,4-bishalobenzene derivative represented by general formula (5):

[Formula 5]

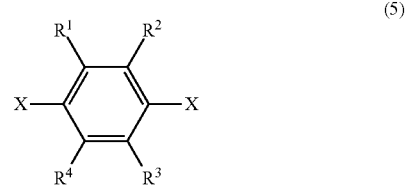

wherein X is iodine and/or bromine, $R^1$ to $R^4$ each independently represent a hydrogen atom, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkyl group having 1 to 2 carbon atoms, a fluorine-containing linear or branched alkoxy group having 3 to 4 carbon atoms, or a halogen atom, provided that $R^1$ to $R^4$ are not all hydrogen atoms; and one or both of ortho positions to an X group is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom; and a compound obtained by reacting 1,1,1,2-tetrafluoroethane, a zinc halide, and an organolithium compound and represented by general formula (4):

[Formula 4]

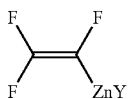

(4)

wherein Y represents chlorine, bromine, or iodine, to obtain a substituted bis(trifluorovinyl)benzene compound represented by general formula (2).

Specific examples of the bishalobenzene derivative represented by general formula (3) used in the method for producing a substituted bis(trifluorovinyl)benzene compound represented by general formula (1) or (2) of the present invention include the following compounds.

Specifically, examples thereof include 1,4-diiodo-2,5-dimethylbenzene 1,4-dibromo-2,5-dimethylbenzene, 1,4-dibromo-2,5-bis(trifluoromethyl)benzene, 1,4-dibromo-2,5-bis(difluoromethyl)benzene, 1,4-dibromo-2,5-bis(pentafluoroethyl)benzene, 1,4-dibromo-2,5-bis(perfluorobutyl) benzene, 1,4-dibromo-2,5-dimethoxybenzene, 1,4-dibromo-2,5-bis(trifluoroethoxy)benzene, 1,4-dibromo-2,5-difluorobenzene, 1,4-dibromo-2,5-dichlorobenzene, 1,4-diiodo-2,3-dimethylbenzene, 1,4-dibromo-2,3-dimethylbenzene, 1,4-dibromo-2,3,5-trimethylbenzene, 1,4-dibromo-2,3,5-trifluorobenzene, 1,4-diiodo-2,3,5,6-tetramethylbenzene, 1,4-dibromo-2,3,5,6-tetramethylbenzene, 1,3-dibromo-4,6-dimethylbenzene, 1,3-dibromo-2,4-dimethylbenzene, 1,3-dibromo-2,5-dimethylbenzene, 1,3-dibromo-4,5,6-trimethylbenzene, 1,3-dibromo-2,4,5-trimethylbenzene, 1,3-dibromo-2,4,5,6-tetramethylbenzene, 1,3-dibromo-4,6-difluorobenzene, 1,3-dibromo-2,4,5,6-fluorobenzene, 1,3-dibromo-4-chloro-6-fluorobenzene, 1,3-diiodo-2-methylbenzene, 1,3-dibromo-2-methylbenzene, 1,3-diiodo-2-fluorobenzene, 1,3-dibromo-2-fluorobenzene, 1,3-dibromo-5-fluoro-2-(trifluoromethyl)benzene, 1,3-dibromo-5-fluoro-2-(difluoromethyl)benzene, 1,3-dibromo-5-fluoro-2-(pentafluoroethyl)benzene, 1,2-dibromo-4,5-dimethylbenzene, 1,2-dibromo-3,6-dimethylbenzene, 1,2-dibromo-3,5-dimethylbenzene, 1,2-dibromo-4,5-difluorobenzene, 1,2-dibromo-3,5-difluorobenzene, 1,2-dibromo-3,4,5-trimethylbenzene, 1,2-dibromo-3,4,6-trimethylbenzene, 1,2-dibromo-3,4,5,6-tetramethylbenzene, and 1,2-dibromo-3,6-bis(chloromethyl)-4,5-dimethylbenzene.

In the method of the present invention, the compound represented by general formula (4), which is a reactant, is preferably prepared from 1,1,1,2-tetrafluoroethane, a zinc halide, and an organolithium compound in a reactor prior to the reaction with the bishalobenzene derivative represented by general formula (3).

In the method of the present invention, generally, the amount of 1,1,1,2-tetrafluoroethane used (loading ratio) is preferably 2.0-fold to 10.0-fold larger than the amount of the bishalobenzene derivative represented by general formula (3) in terms of moles.

Specific examples of the zinc halide used in the method of the present invention include zinc chloride, zinc bromide, and zinc iodide, and generally, the amount thereof used is preferably 2.0-fold to 10.0-fold larger than the amount of the bishalobenzene derivative represented by general formula (3) in terms of moles.

Specific examples of the organolithium compound used in the method of the present invention include lithium dimethylamide, lithium diethylamide, lithium diisopropylamide, lithium dicyclohexylamide, lithium (2,2,6,6-tetramethylpiperidide), and lithium bis(trimethylsilyl)amide. Generally, the amount thereof used is preferably 3.0-fold to 15.0-fold larger than the amount of the bishalobenzene derivative represented by general formula (3) in terms of moles.

As the catalyst used in the reaction between the bishalobenzene derivative represented by general formula (3) and the reactant represented by general formula (4) in the method of the present invention, a zero-valent palladium catalyst may be used, or a divalent palladium catalyst or a divalent nickel catalyst may be used and allowed to undergo the action of a reducing agent (such as diisobutylaluminum hydride or n-butyllithium) to generate zero-valent palladium or zero-valent nickel in the reaction system. The zero-valent palladium catalyst is preferably used because it does not need any specific treatment.

Specific examples of the palladium catalyst and the nickel catalyst that can be used in the method of the present invention include tetrakis(triphenylphosphine)palladium(0), tris(dibenzylideneacetone)dipalladium(0), dichlorobis(triphenylphosphine)palladium(II), dichlorobis (tricyclohexylphosphine)palladium(II), dichlorobis[1,2-bis(diphenylphosphino)ethane]palladium(II), dichlorobis[1,3-bis(diphenylphosphino)propane]palladium(II), dichlorobis[1,4-bis(diphenylphosphino)butane]palladium(II), dichlorobis[1,5-bis(diphenylphosphino)pentane]palladium(II), dichlorobis(triphenylphosphine)nickel(II), dichlorobis[1,2-bis(diphenylphosphino)ethane]palladium(II), dichlorobis[1,3-bis(diphenylphosphino)propane]palladium(II), dichlorobis[1,4-bis(diphenylphosphino)butane]palladium(II), and dichlorobis[1,5-bis(diphenylphosphino)pentane]palladium(II).

Generally, the amount of the catalyst used is preferably 10000-fold to 1-fold smaller than the amount of the bishalobenzene derivative represented by general formula (3) in terms of moles.

In the reaction between the bishalobenzene derivative represented by general formula (3) and the reactant represented by general formula (4) and the preceding reaction for preparing the reactant represented by general formula (4), a solvent to be used is preferably a mixed solvent of an ether solvent and a hydrocarbon solvent.

Specific examples of the ether solvent include tetrahydrofuran (THF), 1,4-dioxane, 1,3-dioxolane, and diethyl ether, and generally, the amount thereof used is preferably 1-fold to 300-fold larger than the amount of the bishalobenzene derivative represented by general formula (3) in terms of weight.

Specific examples of the hydrocarbon solvent include n-hexane, n-heptane, n-pentane, benzene, toluene, and ethylbenzene, and a mixed solvent of two of these listed hydrocarbon solvents may also be used. Generally, the amount used is preferably 1-fold to 300-fold larger than the amount of the bishalobenzene derivative represented by general formula (3) in terms of weight.

In the method of the present invention, generally, the reaction temperature is preferably within the range from 10° C. to 100° C. and is preferably equal to or lower than the boiling point of the solvent used, in the reaction between the bishalobenzene derivative represented by general formula (3) and the reactant represented by general formula (4). Generally, the reaction temperature is preferably within the range from −80° C. to 40° C. and is preferably equal to or higher than the melting point of the solvent used, in the preceding reaction for preparing the reactant represented by general formula (4).

In the reaction between the bishalobenzene derivative represented by general formula (3) and the reactant represented by general formula (4) in the method of the present invention, the amounts of the substrate, the reactant, the catalyst, and the solvent subjected to the reaction and the substrate content can be appropriately set and the reaction time can be determined, according to the type of the leaving group X of the substrate subjected to the reaction. Generally, the preceding reaction for preparing the reactant represented by general formula (4) is carried out for one minute or more after sequentially loading the solvent, the zinc halide, 1,1,1,2-tetrafluoroethane, and the lithium amide compound that are used for the reaction, and the reaction time is preferably within the range from 1 minute to 24 hours.

The substituted bis(trifluorovinyl)benzene compound represented by general formula (1) of the present invention produced can be subjected to a finishing treatment according to any well-known method, for example, in the following manner: the reaction liquid is cooled; an aqueous solution of an acid such as hydrochloric acid is then added thereto; the organic layer is washed with brine etc. and brought into contact with a desiccant such as anhydrous magnesium sulfate to dry; and then the filtrate is concentrated, for example, under reduced pressure to obtain a crude product. The crude product including the objective product can be subjected to purification using a known purifying technique such as recrystallization or silica gel chromatography.

<Stabilization of Substituted Bis(Trifluorovinyl)Benzene Compound of Present Invention>

The substituted bis(trifluorovinyl)benzene compound of the present invention exhibits much higher heat-resistance in the cyclization reaction by heating. The substituted bis (trifluorovinyl)benzene compound of the present invention is so stable that the initial exothermic onset temperature is especially high or cannot be observed in a heating test using, for example, a differential scanning calorimetry (DSC), as compared to compounds that do not fall within the scope of the present invention, e.g., 1,4-bis(trifluorovinyl)benzene, which is a comparative compound in Examples below.

For example, the substituted bis(trifluorovinyl)benzene compound of the present invention exhibits no big change in the purity at room temperature (22 to 28° C.) for at least one mouth, and also is stable in frozen condition for one year or more.

EXAMPLES

The present invention will be described in more detail with reference to the following Examples, but the present invention is not limited to these Examples.

For analysis, the following instruments were used.

$^1$14-NMR, $^{19}$F-NMR: AVANCE II 400 made by BRUKER

GC-MS: GCMS-QP 2010 Plus made by Shimadzu Corporation

Melting point: Melting point Apparatus Model B-545 made by Sibata Scientific Technology Ltd.

DSC apparatus: Thermo Plus 2 series Differential Scanning calorimeter DSC8230 made by Rigaku Corporation

[Example 1] Synthesis of 1,4-bis(trifluorovinyl)-2,3,5,6,-tetramethylbenzene [Compound 1]

[Formula 14]

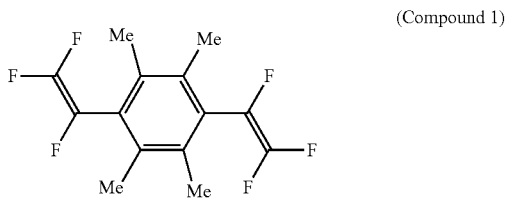

(Compound 1)

A 200 mL four-neck flask equipped with a stirrer was charged with zinc chloride (7.00 g, 51.4 mmol) and tetrahydrofuran (70 mL) under nitrogen atmosphere, and with stirring, 1,1,1,2-tetrafluoroethane (7.70 g, 75.5 mmol) was blown thereinto at −20° C. Next, a tetrahydrofuran-n-hexane solution of lithium diisopropylamide (1.1 M, 99 mL, 108.5 mmol) was gradually added thereto with the dropping port dipped in the liquid content, and the mixture was stirred at room temperature for 30 minutes.

Subsequently, 1,4-diiodo-2,3,5,6-tetramethylbenzene (5.41 g, 14.0 mmol) and tetrakis(triphenylphosphine)palladium (0.65 g, 0.6 mmol) were introduced thereinto and the mixture was stirred at 50° C. for 48 hours. After cooling, an aqueous hydrochloric acid solution was added thereto and the organic layer was washed with 20% saline (50 mL×3 times). The resulting organic layer was dried over anhydrous magnesium sulfate and then the filtrate was concentrated under reduced pressure. The concentrate obtained was purified by silica gel chromatography to give 3.18 g of white solid 1,4-bis(trifluorovinyl)-2,3,5,6-tetramethylbenzene (purity=95.7 wt %, isolated yield=74%).

(Results of Analysis)

$^1$H-NMR (Acetone-d6, 400 MHz); 2.18 ppm (d, 12H, Me).

$^{19}$F-NMR (Acetone-d6, 376 MHz); −158.9 ppm (dd, 2F), −118.3 ppm (ddd, 2F), −104.8 ppm (ddd, 2F).

m.p. 91-94° C.

GC-MS (m/z): 294 (m, 60), 279 (15), 259 (5), 243 (100), 228 (9), 177 (15), 159 (9), 133 (6), 51 (8).

[Example 2] Synthesis of 1,4-bis(trifluorovinyl)-2,5-dimethylbenzene [Compound 2]

[Formula 15]

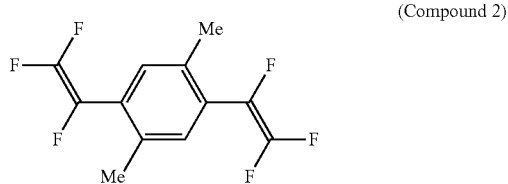

(Compound 2)

A 300 mL four-neck flask equipped with a stirrer was charged with zinc chloride (10.00 g, 73.4 mmol) and tetrahydrofuran (100 mL) under nitrogen atmosphere, and with stirring, 1,1,1,2-tetrafluoroethane (11.50 g, 112.7 mmol) was blown thereinto at −20° C. Next, a tetrahydrofuran-n-hexane solution of lithium diisopropylamide (1.1 M, 141 mL, 155.1 mmol) was gradually added thereto with the dropping port dipped in the liquid content, and the mixture was stirred at room temperature for 30 minutes.

Subsequently, 1,4-dibromo-2,5-dimethylbenzene (5.30 g, 20.1 mmol) and tetrakis(triphenylphosphine)palladium (2.33 g, 2.0 mmol) were introduced thereinto and the mixture was stirred at 60° C. for 24 hours. After cooling, an aqueous hydrochloric acid solution was added thereto and the organic layer was washed with 20% saline (70 mL×3 times). The resulting organic layer was dried over anhydrous magnesium sulfate and then the filtrate was concentrated under reduced pressure. The concentrate obtained was purified by silica gel chromatography to give 3.83 g of 1,4-bis(trifluorovinyl)-2,5-dimethylbenzene in the form of colorless transparent wax at room temperature (purity=99.5 wt %, isolated yield=69%).

(Results of Analysis)
$^1$H-NMR (Acetone-d6, 400 MHz); 2.39 (d, 6H, Me), 7.45 (s, 2H).
$^{19}$F-NMR (Acetone-d6, 376 MHz); −162.4 ppm (dd, 2F), −116.5 ppm (dd, 2F), −102.1 ppm (dd, 2F).
m.p. 20-24° C.
GC-MS (m/z): 266 (m, 100), 251 (10), 245 (9), 231 (21), 215 (58), 195 (27), 182 (19), 177 (18), 162 (21), 151 (20).

[Example 3] Synthesis of 1,4-bis(trifluorovinyl)-2,5-difluorobenzene [Compound 3]

[Formula 16]

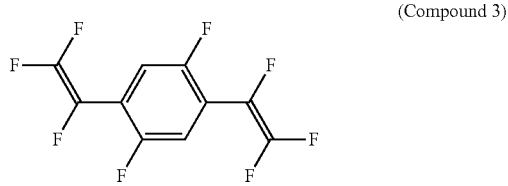

(Compound 3)

A 300 mL four-neck flask equipped with a stirrer was charged with zinc chloride (10.00 g, 73.4 mmol) and tetrahydrofuran (99 mL) under nitrogen atmosphere, and with stirring, 1,1,1,2-tetrafluoroethane (11.00 g, 107.8 mmol) was blown thereinto at −20° C. Next, a tetrahydrofuran-n-hexane solution of lithium diisopropylamide (1.1 M, 140 mL, 154.0 mmol) was gradually added thereto with the dropping port dipped in the liquid content, and the mixture was stirred at room temperature for 30 minutes.

Subsequently, 1,4-dibromo-2,5-difluorobenzene (5.45 g, 20.0 mmol) and tetrakis(triphenylphosphine)palladium (2.33 g, 2.0 mmol) were introduced thereinto and the mixture was stirred at 60° C. for 30 hours. After cooling, an aqueous hydrochloric acid solution was added thereto and the organic layer was washed with 20% saline (70 mL×3 times). The resulting organic layer was dried over anhydrous magnesium sulfate and then the filtrate was concentrated under reduced pressure. The concentrate obtained was purified by silica gel chromatography to give 0.66 g of 1,4-bis(trifluorovinyl)-2,5-difluorobenzene in the form of yellow oil (purity=94.6 wt %, isolated yield=11%).

(Results of Analysis)
$^1$H-NMR (Acetone-d6, 400 MHz); 7.60 (d, 2H).
$^{19}$F-NMR (Acetone-d6, 376 MHz); −171.4 ppm (ddd, 2F), −112.1 ppm (ddd, 2F), −116.6 ppm (m, 2F), −98.4 ppm (dd, 2F).
GC-MS (m/z): 274 (m, 14), 273 (m, 100), 254 (15), 242 (5), 224 (15), 223 (12), 205 (10), 204 (70), 185 (5), 174 (24).

[Example 4] Synthesis of 1,4-bis(trifluorovinyl)-2,5-bis(trifluoromethyl)benzene [Compound 4]

[Formula 17]

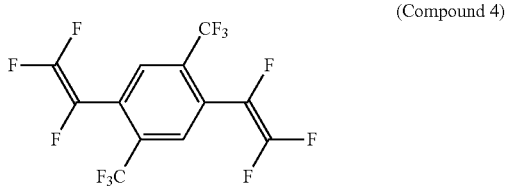

(Compound 4)

A 500 mL four-neck flask equipped with a stirrer was charged with copper iodide (22.80 g, 119.7 mmol), potassium fluoride (7.00 g, 120.5 mmol), 1,10-phenanthroline (0.72 g, 4.6 mmol) and N,N-dimethylformamide (275 mL) under nitrogen atmosphere, and with stirring, trifluoromethyl trimethylsilane (14.4 g, 101.3 mmol) was gradually added thereto at 30 to 40° C., and the mixture was stirred at 35° C. for 1 hour.

Next, a N,N-dimethylformamide solution (80 mL) in which 2,5-dibromo-1,4-diiodobenzene (19.40 g, 39.8 mmol) was dissolved was added thereto and the mixture was stirred at 60° C. for 3 hours. After cooling, an aqueous hydrochloric acid solution, n-hexene and ethyl acetate were added thereto to perform extraction, and the organic layer was washed with a 20% aqueous ammonium chloride solution (100 mL×3 times). The resulting organic layer was dried over anhydrous magnesium sulfate and then the filtrate was concentrated under reduced pressure. The concentrate obtained was purified by silica gel chromatography to give 13.4 g of white solid 1,4-dibromo-2,5-bis(trifluoromethyl)benzene (purity=99.7 wt %, isolated yield=90%).

Compound 4 was synthesized as described below using 1,4-dibromo-2,5-bis(trifluoromethyl)benzene obtained. A 300 mL four-neck flask equipped with a stirrer was charged with zinc chloride (10.00 g, 73.4 mmol) and tetrahydrofuran (99 mL) under nitrogen atmosphere, and with stirring, 1,1,1,2-tetrafluoroethane (11.00 g, 107.8 mmol) was blown thereinto at −20° C. Next, a tetrahydrofuran-n-hexane solution of lithium diisopropylamide (1.1 M, 141 mL, 155.1 mmol) was gradually added thereto with the dropping port dipped in the liquid content, and the mixture was stirred at room temperature for 30 minutes. Subsequently, 1,4-dibromo-2,5-bis(trifluoromethyl)benzene (7.45 g, 20.0 mmol) and tetrakis(triphenylphosphine)palladium (2.33 g, 2.0 mmol) were introduced thereinto and the mixture was stirred at 50° C. for 16 hours. After cooling, an aqueous hydrochloric acid solution was added thereto and the organic layer was washed with 20% saline (70 mL×3 times). The resulting organic layer was dried over anhydrous magnesium sulfate and then the filtrate was concentrated under reduced pressure. The concentrate obtained was purified by silica gel chromatography to give 0.84 g of light yellow solid 1,4-bis(trifluorovinyl)-2,5-bis(trifluoromethyl)benzene (purity=95.2 wt %, isolated yield=11%).

(Results of Analysis)

$^1$H-NMR (Acetone-d6, 400 MHz); 8.44 ppm (s, 2H).

$^{19}$F-NMR (Acetone-d6, 376 MHz); −163.3 ppm (ddt, 2F), −114.4 ppm (dd, 2F), −99.2 ppm (dd, 2F), −62.1 (d, CF3).

m.p. 48-51° C.

GC-MS (m/z): 374 (m, 92), 355 (45), 324 (85), 305 (55), 285 (18), 274 (10), 255 (100), 236 (44), 205 (50), 186 (15), 137 (25), 69 (18).

[Example 5] Synthesis of 1,4-bis(trifluorovinyl)-2,5-dimethoxybenzene [Compound 5]

[Formula 18]

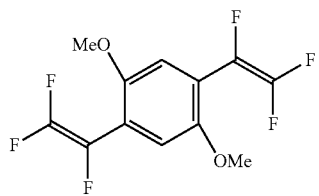

(Compound 5)

A 300 mL four-neck flask equipped with a stirrer was charged with zinc chloride (12.34 g, 90.5 mmol) and tetrahydrofuran (128 mL) under nitrogen atmosphere, and with stirring, 1,1,1,2-tetrafluoroethane (13.86 g, 135.8 mmol) was blown thereinto at −20° C. Next, a tetrahydrofuran-n-hexane solution of lithium diisopropylamide (1.1 M, 162 mL, 178.2 mmol) was gradually added thereto with the dropping port dipped in the liquid content, and the mixture was stirred at room temperature for 30 minutes.

Subsequently, 1,4-dibromo-2,5-dimethoxybenzene (6.83 g, 23.1 mmol) and tetrakis(triphenylphosphine)palladium (2.53 g, 2.2 mmol) were introduced thereinto and the mixture was stirred at 50 to 55° C. for 17 hours. After cooling, an aqueous hydrochloric acid solution was added thereto and the organic layer was washed with 20% saline (80 mL×3 times). The resulting organic layer was dried over anhydrous magnesium sulfate and then the filtrate was concentrated under reduced pressure. The concentrate obtained was purified by silica gel chromatography to give 5.32 g of white solid 1,4-bis(trifluorovinyl)-2,5-dimethoxybenzene (purity=99.6 wt %, isolated yield=77%).

(Results of Analysis)

$^1$H-NMR (Acetone-d6, 400 MHz); 3.91 ppm (s, 6H, OMe), 7.26 ppm (s, 2H).

$^{19}$F-NMR (Acetone-d6, 376 MHz); −165.7 ppm (dd, 2F), −115.3 ppm (ddd, 2F), −102.8 ppm (ddd, 2F).

m.p. 68-70° C.

GC-MS (m/z): 299 (m+1, 12), 298 (m, 100), 283 (35), 268 (55), 249 (6), 240 (30), 232 (9), 212 (20), 204 (13), 162 (15), 143 (13), 106 (20).

[Example 6] Synthesis of 1,3-bis(trifluorovinyl)-4,6-dimethylbenzene [Compound 6]

[Formula 19]

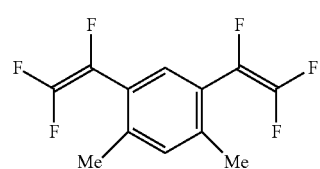

(Compound 6)

A 300 mL four-neck flask equipped with a stirrer was charged with zinc chloride (7.50 g, 55.0 mmol) and tetrahydrofuran (122 mL) under nitrogen atmosphere, and with stirring, 1,1,1,2-tetrafluoroethane (9.40 g, 92.1 mmol) was blown thereinto at −20° C. Next, a tetrahydrofuran-n-hexane solution of lithium diisopropylamide (1.1 M, 118 mL, 129.4 mmol) was gradually added thereto with the dropping port dipped in the liquid content, and the mixture was stirred at room temperature for 30 minutes.

Subsequently, 1,3-diiodo-4,6-methylbenzene (4.87 g, 13.6 mmol) and tetrakis(triphenylphosphine)palladium (0.87 g, 0.75 mmol) were introduced thereinto and the mixture was stirred at 50° C. for 16 hours. After cooling, an aqueous hydrochloric acid solution was added thereto and the organic layer was washed with 20% saline (80 mL×3 times). The resulting organic layer was dried over anhydrous magnesium sulfate and then the filtrate was concentrated under reduced pressure. The concentrate obtained was purified by silica gel chromatography to give 2.80 g of 1,3-bis(trifluorovinyl)-4,6-dimethylbenzene in the form of colorless transparent oil (purity=97.2 wt %, isolated yield=75%).

(Results of Analysis)

$^1$H-NMR (Acetone-d6, 400 MHz); 2.40 ppm (s, 6H, Me), 7.37 ppm (s, 1H), 7.49 ppm (s, 1H).

$^{19}$F-NMR (Acetone-d6, 376 MHz); −162.2 ppm (dd, 2F), −118.3 ppm (dd, 2F), −103.6 ppm (dd, 2F).

GC-MS (m/z): 267 (m+1, 12), 266 (m, 100), 251 (8), 245 (10), 231 (20), 215 (70), 197 (15), 195 (30), 182 (21), 177 (22), 175 (15), 169 (15), 164 (23), 151 (20), 146 (15).

[Example 7] Synthesis of 1,3-bis(trifluorovinyl)-2-methylbenzene [Compound 7]

[Formula 20]

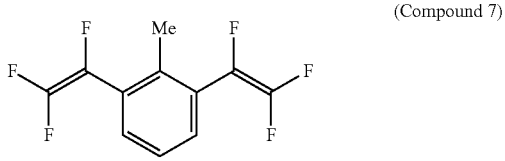

(Compound 7)

A 300 mL four-neck flask equipped with a stirrer was charged with zinc chloride (11.10 g, 81.4 mmol) and tetrahydrofuran (140 mL) under nitrogen atmosphere, and with stirring, 1,1,1,2-tetrafluoroethane (13.14 g, 128.8 mmol) was blown thereinto at −20° C. Next, a tetrahydrofuran-n-hexane solution of lithium diisopropylamide (1.1 M, 157 mL, 173.0 mmol) was gradually added thereto with the dropping port dipped in the liquid content, and the mixture was stirred at room temperature for 30 minutes.

Subsequently, 1,3-dibromo-2-methylbenzene (5.00 g, 20.0 mmol) and tetrakis(triphenylphosphine)palladium (2.40 g, 2.1 mmol) were introduced thereinto and the mixture was stirred at 55 to 65° C. for 48 hours. After cooling, an aqueous hydrochloric acid solution was added thereto and the organic layer was washed with 20% saline (80 mL×3 times). The resulting organic layer was dried over anhydrous magnesium sulfate and then the filtrate was concentrated under reduced pressure. The concentrate obtained was purified by silica gel chromatography to give 2.29 g of 1,3-bis(trifluorovinyl)-2-methylbenzene in the form of yellow transparent oil (purity=94.3 wt %, isolated yield=43%).

(Results of Analysis)
$^1$H-NMR (Acetone-d6, 400 MHz); 2.42 ppm (s, 6H, Me), 7.48 ppm (t, 1H), 7.64 ppm (d, 2H).
$^{19}$F-NMR (Acetone-d6, 376 MHz); −161.5 ppm (dd, 2F), −117.8 ppm (dd, 2F), −103.2 ppm (dd, 2F).
GC-MS (m/z): 252 (m, 60), 201 (70), 183 (30), 182 (40), 181 (15), 151 (100), 133 (33), 75 (25), 69 (35).

[Example 8] Synthesis of 1,3-bis(trifluorovinyl)-5-fluoro-2-difluoromethoxybenzene [Compound 8]

[Formula 21]

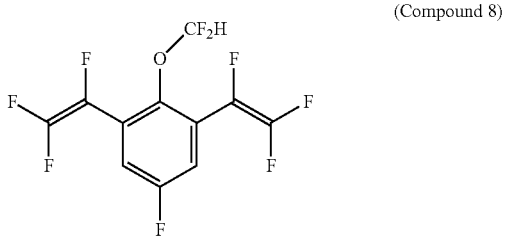

(Compound 8)

A 300 mL four-neck flask equipped with a stirrer was charged with potassium hydroxide (35.78 g, 637.7 mmol) and water (122 mL) under nitrogen atmosphere and the component was dissolved. Then, with stirring at 10° C. or less, a mixed solution of 2,6-dibromo-4-fluorophenol (6.46 g, 23.9 mmol) and acetonitrile (122 mL) was added thereto. After stirring for 15 minutes, the mixture was cooled to −20° C. or less, and diethyl (bromodifluoromethyl)phosphonate (9.80 g, 36.7 mmol) was gradually added dropwise thereto. After completing the dropwise addition, the temperature of the mixture was increased to room temperature and the mixture was stirred for 2 hours. Then the mixture was extracted with methyl t-butyl ether (50 mL×3 times), and the organic layer was washed with a 20% aqueous ammonium chloride solution (50 mL×3 times). The resulting organic layer was dried over anhydrous magnesium sulfate and then the filtrate was concentrated under reduced pressure to give 7.84 g of light yellow solid 1,3-dibromo-5-fluoro-2-difluoromethoxybenzene (purity=97.5 wt %, isolated yield=98%).

Compound 8 was synthesized as described below using 1,3-dibromo-5-fluoro-2-difluoromethoxybenzene obtained. A 300 mL four-neck flask equipped with a stirrer was charged with zinc chloride (8.16 g, 59.9 mmol) and tetrahydrofuran (96 mL) under nitrogen atmosphere, and with stirring, 1,1,1,2-tetrafluoroethane (9.78 g, 95.9 mmol) was blown thereinto at −20° C. Next, a tetrahydrofuran-n-hexane solution of lithium diisopropylamide (1.1 M, 111 mL, 122.1 mmol) was gradually added thereto with the dropping port dipped in the liquid content, and the mixture was stirred at room temperature for 30 minutes. Subsequently, 1,3-dibromo-5-fluoro-2-difluoromethoxybenzene (4.85 g, 97.5 wt %, 14.8 mmol) and tetrakis(triphenylphosphine)palladium (1.75 g, 1.5 mmol) were introduced thereinto and the mixture was refluxed for 70 hours. After cooling, an aqueous hydrochloric acid solution was added thereto and the organic layer was washed with 20% saline (50 mL×3 times). The resulting organic layer was dried over anhydrous magnesium sulfate and then the filtrate was concentrated under reduced pressure. The concentrate obtained was purified by silica gel chromatography to give 0.86 g of 1,3-bis(trifluorovinyl)-5-fluoro-2-difluoromethoxybenzene in the form of yellow transparent oil (purity=95.0 wt %, isolated yield=17%).

(Results of Analysis)
$^1$H-NMR (Acetone-d6, 400 MHz); 6.88 ppm (t, 1H, CF2H), 7.60 (d, 2H).
$^{19}$F-NMR (Acetone-d6, 376 MHz); −168.4 ppm (dd, 2F), −113.9 ppm (dd, 2F), −113.5 ppm (t, 1F), −100.2 (dd, 2F), −82.2 (d, 2F, CF2H).
GC-MS (m/z): 323 (m+1, 10), 322 (m, 80), 272 (30), 271 (60), 253 (85), 252 (55), 225 (100), 224 (35), 205 (90), 193 (50), 174 (80), 143 (60), 51 (85).

[Example 9] Synthesis of 1,2-bis(trifluorovinyl)-4,5-difluorobenzene [Compound 9]

[Formula 22]

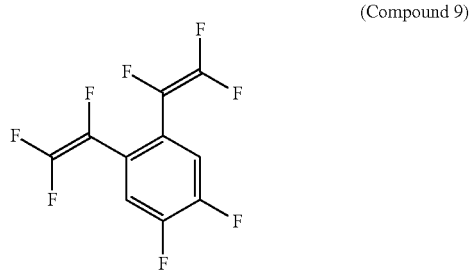

(Compound 9)

A 300 mL four-neck flask equipped with a stirrer was charged with zinc chloride (12.36 g, 90.7 mmol) and tetrahydrofuran (97 mL) under nitrogen atmosphere, and with stirring, 1,1,1,2-tetrafluoroethane (13.92 g, 136.4 mmol) was blown thereinto at −20° C. Next, a tetrahydrofuran-n-hexane solution of lithium diisopropylamide (1.1 M, 163 mL, 179.3 mmol) was gradually added thereto with the dropping port dipped in the liquid content, and the mixture was stirred at room temperature for 30 minutes. Subsequently, 1,2-dibromo-4,5-difluorobenzene (5.44 g, 20.0 mmol) and tetrakis(triphenylphosphine)palladium (2.58 g, 2.2 mmol) were introduced thereinto and the mixture was refluxed for 66 hours. After cooling, an aqueous hydrochloric acid solution was added thereto and the organic layer was washed with 20% saline (50 mL×3 times). The resulting organic layer was dried over anhydrous magnesium sulfate and then the filtrate was concentrated under reduced pressure. The concentrate obtained was purified by silica gel chromatography to give 1.31 g of 1,2-bis(trifluorovinyl)-4,5-difluorobenzene in the form of yellow transparent oil (purity=93.6 wt %, isolated yield=22%).

(Results of Analysis)
$^{1}$H-NMR (Acetone-d6, 400 MHz); 7.78 ppm (t, 2H).
$^{19}$F-NMR (Acetone-d6, 376 MHz); −166.9 ppm (ddd, 2F), −133.4 ppm (d, 2F), −116.3 ppm (dd, 2F), −100.8 (dd, 2F).
GC-MS (m/z): 275 (m+1, 3), 274 (m, 25), 255 (8), 236 (3), 224 (12), 223 (13), 205 (100), 185 (6), 174 (15), 155 (3), 124 (6), 105 (7).

[Example 10] Synthesis of 1,2-bis(trifluorovinyl)-3,5-difluorobenzene [Compound 10]

[Formula 23]

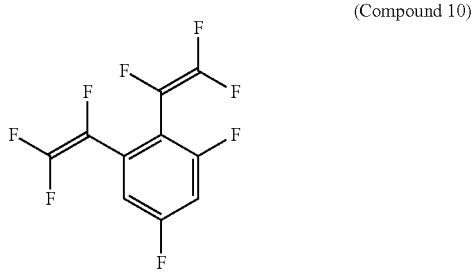

(Compound 10)

A 100 mL four-neck flask equipped with a stirrer was charged with zinc chloride (2.40 g, 17.6 mmol) and tetrahydrofuran (25 mL) under nitrogen atmosphere, and with stirring, 1,1,1,2-tetrafluoroethane (2.52 g, 24.7 mmol) was blown thereinto at −20° C. Next, a tetrahydrofuran-n-hexane solution of lithium diisopropylamide (1.1 M, 25 mL, 27.5 mmol) was gradually added thereto with the dropping port dipped in the liquid content, and the mixture was stirred at room temperature for 60 minutes. Subsequently, 1,2-dibromo-3,5-difluorobenzene (0.99 g, 3.6 mmol) and tetrakis(triphenylphosphine)palladium (0.45 g, 0.39 mmol) were introduced thereinto and the mixture was refluxed for 70 hours. After cooling, an aqueous hydrochloric acid solution was added thereto and the organic layer was washed with 20% saline (50 mL×3 times). The resulting organic layer was dried over anhydrous magnesium sulfate and then the filtrate was concentrated under reduced pressure. The concentrate obtained was purified by silica gel chromatography to give 0.15 g of 1,2-bis(trifluorovinyl)-3,5-difluorobenzene in the form of colorless transparent oil (purity=94.1 wt %, isolated yield=14%).

(Results of Analysis)
$^{1}$H-NMR (Acetone-d6, 400 MHz); 7.53 ppm (m, 1H), 7.65 (m, 1H).
$^{19}$F-NMR (Acetone-d6, 376 MHz); −176.4 ppm (dd, 1F), −170.7 ppm (ddd, 1F), −135.6 ppm (m, 2F), −113.2 (m, 1F), −113.0 (dd, 1F), −98.8 ppm (m, 2F).
GC-MS (m/z): 275 (m+1, 12), 274 (m, 100), 255 (15), 243 (6), 236 (2), 224 (12), 223 (13), 206 (12), 205 (90), 185 (6), 174 (20), 155 (5), 137 (11), 124 (7), 105 (11).

[Comparative Example 1] Synthesis of 1,4-bis(trifluorovinyl)benzene [Comparative Compound 1]

[Formula 24]

(Comparative Compound 1)

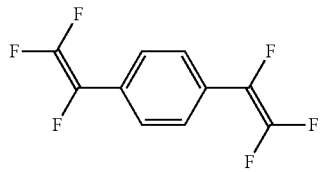

A 300 mL four-neck flask equipped with a stirrer was charged with zinc chloride (10.00 g, 73.4 mmol) and tetrahydrofuran (100 mL) under nitrogen atmosphere, and with stirring, 1,1,1,2-tetrafluoroethane (11.00 g, 107.8 mmol) was blown thereinto at −20° C. Next, a tetrahydrofuran-n-hexane solution of lithium diisopropylamide (1.1 M, 141 mL, 155.1 mmol) was gradually added thereto with the dropping port dipped in the liquid content, and the mixture was stirred at room temperature for 30 minutes.

Subsequently, 1,4-diiodobenzene (6.60 g, 20.0 mmol) and tetrakis(triphenylphosphine)palladium (0.93 g, 0.8 mmol) were introduced thereinto and the mixture was stirred at 30° C. for 1 hour. After cooling, an aqueous hydrochloric acid solution was added thereto and the organic layer was washed with 20% saline (70 mL×3 times). The resulting organic layer was dried over anhydrous magnesium sulfate and then the filtrate was concentrated under reduced pressure. The concentrate obtained was purified by silica gel chromatography to give 3.11 g of 1,4-bis(trifluorovinyl)benzene in the form of colorless transparent oil at room temperature (purity=96.3 wt %, isolated yield=63%).

[Comparative Example 2] Synthesis of 1,3-bis(trifluorovinyl)benzene [Comparative Compound 2]

[Formula 25]

(Comparative Compound 2)

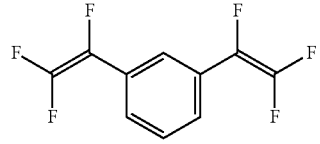

A 300 mL four-neck flask equipped with a stirrer was charged with zinc chloride (10.80 g, 79.2 mmol) and tetrahydrofuran (126 mL) under nitrogen atmosphere, and with stirring, 1,1,1,2-tetrafluoroethane (12.66 g, 124.1 mmol) was blown thereinto at −20° C. Next, a tetrahydrofuran-n-hexane solution of lithium diisopropylamide (1.1 M, 147 mL, 161.7 mmol) was gradually added thereto with the dropping port dipped in the liquid content, and the mixture was stirred at room temperature for 30 minutes.

Subsequently, 1-bromo-3-iodobenzene (6.30 g, 22.2 mmol) and tetrakis(triphenylphosphine)palladium (2.74 g, 2.4 mmol) were introduced thereinto and the mixture was stirred at 30° C. for 1 hour, and then stirred at 60° C. for 26 hours. After cooling, an aqueous hydrochloric acid solution was added thereto and the organic layer was washed with 20% saline (70 mL×3 times). The resulting organic layer was dried over anhydrous magnesium sulfate and then the filtrate was concentrated under reduced pressure. The concentrate obtained was purified by silica gel chromatography to give 2.18 g of 1,3-bis(trifluorovinyl)benzene in the form of yellow transparent oil at room temperature (purity=95.4 wt %, isolated yield=39%).

[Example 11] Measurement of Cyclodimerization Starting Temperature by DSC Measurement The substituted bis(trifluorovinyl)benzene compound of the present invention or Comparative Compound 1 was weighed and put in a DSC cell made of SUS under nitrogen atmosphere and the cell was sealed. The resulting samples were subjected to DSC measurement in the range of measurement temperature of 30° C. to 400° C. at a temperature increasing rate of 10° C./minute. The cyclodimerization temperature or decomposition temperature of each sample is observed as an initial exothermic onset temperature in DSC. Furthermore, since cyclodimerization reaction of trifluorovinyl compounds is known to generate heat, the accelerating rate of cyclodimerization reaction is represented by the amount of heat generated. The respective results are shown in Table 1.

In the case of, for example, compounds in which all of substituents ($R^1$ to $R^4$) are a hydrogen atom as in Comparative Compound 1, a large amount of heat is generated and cyclodimerization is accelerated at about 90° C. In contrast to Comparative Compound 1, the substituted bis(trifluorovinyl)benzene compound of the present invention showed high heat stability, with the initial exothermic onset temperature shifted to the side of high temperature and a decrease in the amount of heat generated.

TABLE 1

| Name of compound | Amount of DSC sample [mg] | DSC initial exothermic onset temperature [° C.] | Amount of heat generated in DSC [KJ · mol⁻¹] |
|---|---|---|---|
| (Compound 1) | 3.3 | 342 | 68.5 |
| (Compound 2) | 3.6 | 201 | 61.0 |
| (Compound 3) | 2.8 | 182 | 35.8 |
| (Compound 4) | 3.4 | N/A | N/A |
| (Compound 5) | 4.8 | 180 | 72.8 |
| (Compound 6) | 1.8 | 140 | 12.9 |
| (Compound 7) | 2.7 | 175 | 5.7 |
| (Compound 8) | 2.8 | 309 | 3.3 |

TABLE 1-continued

| Name of compound | Amount of DSC sample [mg] | DSC initial exothermic onset temperature [° C.] | Amount of heat generated in DSC [KJ·mol⁻¹] |
|---|---|---|---|
| 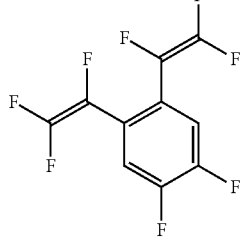 (Compound 9) | 1.2 | 220 | 0.9 |
| 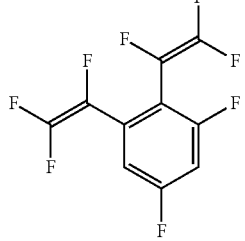 (Compound 10) | 1.1 | 120 | 3.9 |
| 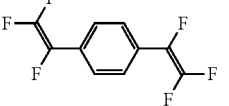 (Comparative Compound 1) | 1.5 | 90 | 95.3 |
| 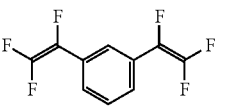 (Comparative Compound 2) | 3.2 | 100 | 79.6 |

[Example 12] Storage Stability Test

The substituted bis(trifluorovinyl)benzene compound of the present invention or Comparative Compound 1 was put in a container made of PE under nitrogen atmosphere and stored for 7 days, 21 days at room temperature (22 to 28° C.), and also for 1 year in a freezer (−18° C.) After storing for the respective days, the purity (percent concentration by weight) was measured with 19F-NMR using an internal standard method. Trifluoromethylbenzene or hexafluorobenzene was used as an internal standard compound.

Although the purity of Comparative Compound 1 was 96% at the beginning of storage, the purity at room temperature decreased to 61% after 7 days, and the purity at −18° C. also decreased to 91% after 1 year. By contrast, the purity at the beginning of storage of the substituted bis(trifluorovinyl)benzene compound of the present invention was substantially kept even after being stored at room temperature for 7 days, 21 days and after being stored frozen for 1 year.

TABLE 2

| | Purity (percent concentration by weight [wt %]) | | | |
|---|---|---|---|---|
| Name of compound | At the beginning of storage | Room temperature (22 to 28° C.) | | Freezer (−18° C.) 1 year |
| | | After 7 days | After 21 days | |
| 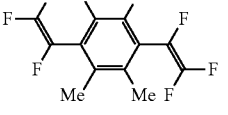 (Compound 1) | 95.7 | 96.1 | 95.7 | 95.6 |
| 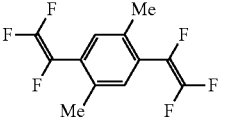 [SMILES: Cc1cc(C(F)=C(F)F)c(C)cc1C(F)=C(F)F] (Compound 2) | 99.5 | 98.9 | 97.5 | 99.7 |
| 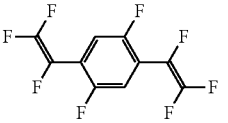 [SMILES: FC(F)=C(F)c1cc(F)c(C(F)=C(F)F)cc1F] (Compound 3) | 94.6 | 96.1 | 94.8 | 94.7 |
| 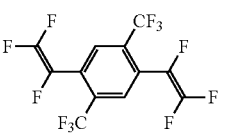 (Compound 4) | 95.2 | 95.3 | 95.2 | 95.1 |
| 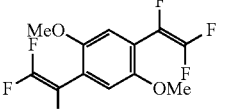 (Compound 5) | 99.6 | 99.7 | 99.6 | 99.6 |
| 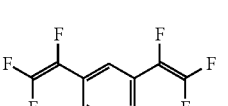 (Compound 6) | 97.2 | 97.1 | 97.1 | 97.2 |
| 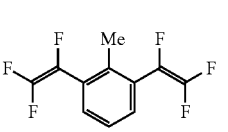 [SMILES: Cc1c(C(F)=C(F)F)cccc1C(F)=C(F)F] (Compound 7) | 94.3 | 93.5 | 93.2 | 93.8 |

TABLE 2-continued

| Name of compound | Purity (percent concentration by weight [wt %]) | | | |
|---|---|---|---|---|
| | At the beginning of storage | Room temperature (22 to 28° C.) After 7 days | After 21 days | Freezer (−18° C.) 1 year |
| (Compound 8) | 95.0 | 94.9 | 94.9 | 94.9 |
| (Compound 9) | 93.6 | 93.6 | 93.5 | 93.4 |
| (Compound 10) | 94.1 | 93.8 | 93.5 | 93.8 |
| (Comparative Compound 1) | 96.3 | 61.3 | 33.4 | 90.9 |
| (Comparative Compound 2) | 95.4 | 83.8 | 69.3 | 92.2 |

INDUSTRIAL APPLICABILITY

The present invention has made available a substituted bis(trifluorovinyl)benzene compound that is excellent in heat stability and is new and useful as a starting material for polymers.

The invention claimed is:

1. A substituted bis(trifluorovinyl)benzene compound represented by general formula (1):

[Formula 1]

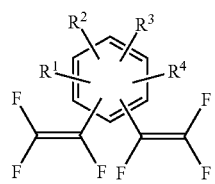

(1)

wherein $R^1$, $R^2$, $R^3$, and $R^4$ are each independently a hydrogen, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom, provided that $R^1$, $R^2$, $R^3$, and $R^4$ are not all hydrogen; and one or both of ortho positions of the benzene ring to a trifluorovinyl group on the benzene ring is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen.

2. A substituted bis(trifluorovinyl)benzene compound represented by general formula (2):

[Formula 2]

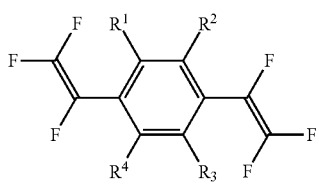

(2)

wherein $R^1$, $R^2$, $R^3$, and $R^4$ are each independently a hydrogen, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen, provided that $R^1$, $R^2$, $R^3$, and $R^4$ are not all hydrogen; and one or both of ortho positions to a trifluorovinyl group on the benzene ring is substituted with a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen atom.

3. The substituted bis(trifluorovinyl)benzene compound according to claim 1, wherein at least one of ortho positions to a trifluorovinyl group is substituted with a methyl group, a trifluoromethyl group, a difluoromethyl group, a pentafluoroethyl group, a methoxy group, or a fluorine atom.

4. The substituted bis(trifluorovinyl)benzene compound according to claim 1, wherein the substituted bis(trifluorovinyl)benzene compound is 1,4-bis(trifluorovinyl)-2,3,5,6,-tetramethylbenzene, 1,4-bis(trifluorovinyl)-2,5-dimethylbenzene, 1,4-bis(trifluorovinyl)-2,5-difluorobenzene, 1,4-bis(trifluorovinyl)-2,5-bis(trifluoromethyl)benzene.

5. A method for producing a substituted bis(trifluorovinyl)benzene compound of claim 1, the method comprising reacting, in the presence of a catalyst, a bishalobenzene derivative represented by general formula (3):

[Formula 3]

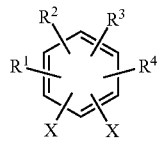
(3)

wherein X is at each occurrence, independently iodine or bromine, $R^1$ $R^2$, $R^3$, and $R^4$ are each independently represent a hydrogen, a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen, provided that $R^1$ $R^2$, $R^3$, and $R^4$ are not all hydrogen atoms; and one or both of ortho positions to an X group is a methyl group, an ethyl group, a linear or branched alkyl group having 3 to 4 carbon atoms, a fluorine-containing alkyl group having 1 to 2 carbon atoms, a fluorine-containing linear or branched alkyl group having 3 to 4 carbon atoms, a fluorine-containing alkenyl group having 2 to 3 carbon atoms, a methoxy group, an ethoxy group, a linear or branched alkoxy group having 3 to 4 carbon atoms, a fluorine-containing alkoxy group having 1 to 2 carbon atoms, a fluorine-containing linear or branched alkoxy group having 3 to 4 carbon atoms, or a halogen;

with a compound represented by general formula (4):

[Formula 4]

(4)

wherein Y is chlorine, bromine, or iodine, to obtain a substituted bis(trifluorovinyl)benzene compound represented by general formula (1)

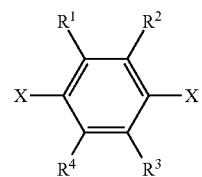
(6)

wherein $R^1$ to $R^4$ are as defined for formula (1).

6. The method of claim 5, wherein the bishalobenzene derivative is a 1,4-bishalobenzene derivative represented by general formula (5):

[Formula 5]

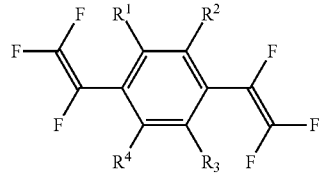
(5)

and the substituted bis(trifluorovinyl)benzene compound is a compound of formula (2)

(2)

wherein $R^1$ to $R^4$ are as defined for formula (2).

7. The method according to claim 5, wherein at least one of ortho positions to a trifluorovinyl group of the substituted bis(trifluorovinyl)benzene compound is substituted with a methyl group, a trifluoromethyl group, a difluoromethyl group, a pentafluoroethyl group, a methoxy group, or a fluorine.

8. The method according to claim 5, wherein the substituted bis(trifluorovinyl)benzene compound is 1,4-bis(trifluorovinyl)-2,3,5,6,-tetramethylbenzene, 1,4-bis(trifluorovinyl)-2,5-dimethylbenzene, 1,4-bis(trifluorovinyl)-2,5-difluorobenzene, or 1,4-bis(trifluorovinyl)-2,5-bis(trifluoromethyl)benzene.

9. The substituted bis(trifluorovinyl)benzene compound according to claim 1, wherein the substituted bis(trifluorovinyl)benzene compound is 1,4-bis(trifluorovinyl)-2,5-dimethoxybenzene.

10. The method according to claim 5, wherein the substituted bis(trifluorovinyl)benzene compound is 1,4-bis(trifluorovinyl)-2,5-dimethoxybenzene.

11. The substituted bis(trifluorovinyl)benzene compound of claim 1, represented by general formulae (8) or (9):

[Formula 8]

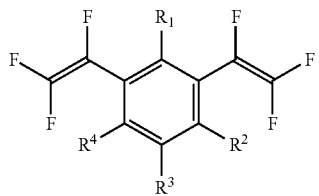

(8)

[Formula 9]

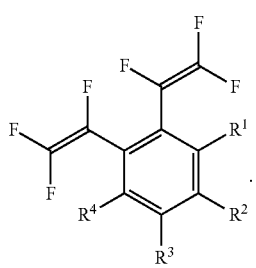

(9)

12. The substituted bis(trifluorovinyl)benzene compound according to claim 1, wherein at least one of ortho positions to a trifluorovinyl group of the substituted bis(trifluorovinyl)benzene compound is substituted with a methyl group, a trifluoromethyl group, a difluoromethyl group, a pentafluoroethyl group, a methoxy group, a difluoromethoxy group, or a fluorine.

13. The substituted bis(trifluorovinyl)benzene compound according to claim 1, wherein the substituted bis(trifluorovinyl)benzene compound is 1,3-bis(trifluorovinyl)-4,6-dimethylbenzene, 1,3-bis(trifluorovinyl)-2-methylbenzene, 1,3-bis(trifluorovinyl)-5-fluoro-2-difluoromethylbenzene, 1,2-bis(trifluorovinyl)-4,5-difluorobenzene, or 1,2-bis(trifluorovinyl)-3,5-difluorobenzene.

14. The method for producing a substituted bis(trifluorovinyl)benzene compound according to claim 5,
wherein the bishalobenzene derivative of formula (3) is represented by formulae (10) or (11):

[Formula 10]

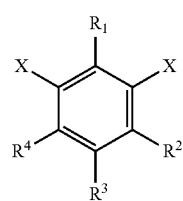

(10)

[Formula 11]

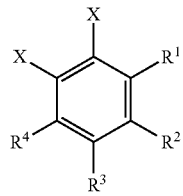

(11)

and the substituted bis(trifluorovinyl)benzene compound of formula (1) obtained is represented by general formulae (12) or (13):

[Formula 12]

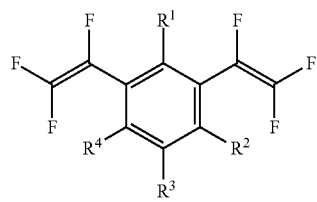

(12)

[Formula 13]

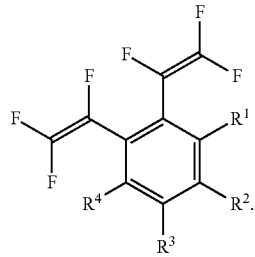

(13)

15. The method according to claim 14, wherein at least one of ortho positions to a trifluorovinyl group of the substituted bis(trifluorovinyl)benzene compound is substituted with a methyl group, a trifluoromethyl group, a difluoromethyl group, a pentafluoroethyl group, a methoxy group, a difluoromethoxy group, or a fluorine.

16. The method according to claim 14, wherein the substituted bis(trifluorovinyl)benzene compound is 1,3-bis(trifluorovinyl)-4,6-dimethylbenzene, 1,3-bis(trifluorovinyl)-2-methylbenzene, 1,3-bis(trifluorovinyl)-5-fluoro-2-difluoromethylbenzene, 1,2-bis(trifluorovinyl)-4,5-difluorobenzene, or 1,2-bis(trifluorovinyl)-3,5-difluorobenzene.

17. The method of claim 5, wherein the method further comprises reacting 1,1,1,2-tetrafluoroethane with a zinc halide, and an organolithium compound thereby producing a compound of formula (4):

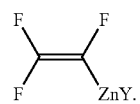

(4)

18. The method of claim 5, wherein the catalyst is a palladium catalyst.

19. The substituted bis(trifluorovinyl)benzene compound according to claim 2, wherein at least one of ortho positions to a trifluorovinyl group is substituted with a methyl group, a trifluoromethyl group, a difluoromethyl group, a pentafluoroethyl group, a methoxy group, or a fluorine atom.

20. The substituted bis(trifluorovinyl)benzene compound according to claim 2, wherein the substituted bis(trifluorovinyl)benzene compound is 1,4-bis(trifluorovinyl)-2,3,5,6,-tetramethylbenzene, 1,4-bis(trifluorovinyl)-2,5-dimethylbenzene, 1,4-bis(trifluorovinyl)-2,5-difluorobenzene, 1,4-bis(trifluorovinyl)-2,5-bis(trifluoromethyl)benzene.

* * * * *